United States Patent
Thörn

(10) Patent No.: US 9,874,872 B2
(45) Date of Patent: Jan. 23, 2018

(54) METHODS AND DEVICES FOR HEART RATE CONTROLLING DRONES

(71) Applicants: Sony Mobile Communications Inc., Tokyo (JP); Sony Corporation, Tokyo (JP)

(72) Inventor: Ola Thörn, Lund (SE)

(73) Assignee: Sony Mobile Communications Inc., Tokyo (JP)

( * ) Notice: Subject to any disclaimer, the term of this patent is extended or adjusted under 35 U.S.C. 154(b) by 0 days.

(21) Appl. No.: 15/343,962

(22) Filed: Nov. 4, 2016

(65) Prior Publication Data
US 2017/0123415 A1 May 4, 2017

Related U.S. Application Data

(63) Continuation of application No. 14/927,506, filed on Oct. 30, 2015, now Pat. No. 9,513,629.

(51) Int. Cl.
*G05D 1/00* (2006.01)
*A61B 5/024* (2006.01)
(Continued)

(52) U.S. Cl.
CPC .......... *G05D 1/0016* (2013.01); *A61B 5/024* (2013.01); *A63B 69/0028* (2013.01);
(Continued)

(58) Field of Classification Search
CPC ...... G05D 1/0016; G05D 1/12; G05D 1/0094; A61B 5/024; A63B 69/0028; B64C 39/024; B64C 2201/127; B64D 47/08
(Continued)

(56) References Cited

U.S. PATENT DOCUMENTS 8,521,352 B1 * 8/2013 Ferguson ............. G05D 1/0274
340/435
9,513,629 B1 * 12/2016 Thorn .................. G05D 1/0016
(Continued)

OTHER PUBLICATIONS

Notification of Transmittal of the International Search Report and the Written Opinion of the International Searching Authority, or the Declaration, PCT/US2016/029312, Jul. 1, 2016, 10 pages.
(Continued)

*Primary Examiner* — Jelani A Smith
*Assistant Examiner* — James E Stroud
(74) *Attorney, Agent, or Firm* — Myers Bigel, P.A.

(57) ABSTRACT

A method for controlling a drone including performing operations on a processor configured to control location of the drone are described. The operations on the processor include receiving heart rate messages from a remote device carried by a user, where each heart rate message includes heart rate information of the user, and receiving location messages from the remote device carried by the user, where each location message includes location information of the user. The method includes predicting a future location of the user based on the heart rate messages and the location messages, generating a target location to which the drone is to be moved based on the future location of the user, and commanding the drone to move to the target location. Related devices are disclosed.

20 Claims, 10 Drawing Sheets

(51) Int. Cl.
    *B64C 39/02*  (2006.01)
    *B64D 47/08*  (2006.01)
    *G05D 1/12*   (2006.01)
    *A63B 69/00*  (2006.01)

(52) U.S. Cl.
    CPC .......... *B64C 39/024* (2013.01); *B64D 47/08*
        (2013.01); *G05D 1/0094* (2013.01); *G05D*
        *1/12* (2013.01); *B64C 2201/127* (2013.01)

(58) Field of Classification Search
    USPC .......................................................... 701/2
    See application file for complete search history.

(56) References Cited

U.S. PATENT DOCUMENTS

| | | | |
|---|---|---|---|
| 2010/0030399 A1* | 2/2010 | Zellner | G08B 25/08 |
| | | | 701/2 |
| 2010/0063652 A1* | 3/2010 | Anderson | A61B 5/02438 |
| | | | 701/2 |
| 2014/0024999 A1 | 1/2014 | Levien et al. | |
| 2014/0283896 A1* | 9/2014 | Lunt, III | H01L 31/055 |
| | | | 136/247 |
| 2014/0209814 A1 | 10/2014 | Ricci | |
| 2014/0209815 A1 | 10/2014 | Ricci | |
| 2014/0309814 A1* | 10/2014 | Ricci | B60Q 1/00 |
| | | | 701/2 |
| 2014/0309815 A1* | 10/2014 | Ricci | H04W 48/04 |
| | | | 701/2 |
| 2014/0371953 A1* | 12/2014 | Miller | B62M 25/08 |
| | | | 701/2 |
| 2015/0081136 A1* | 3/2015 | Sutherland | G08B 21/043 |
| | | | 701/2 |
| 2015/0183498 A1 | 7/2015 | Wardle | |
| 2015/0352997 A1 | 12/2015 | Sutherland | |
| 2015/0362997 A1* | 12/2015 | Hatton | G60F 3/017 |
| | | | 701/2 |
| 2016/0009337 A1* | 1/2016 | Biderman | B60L 15/20 |
| | | | 701/2 |
| 2016/0139594 A1* | 5/2016 | Okumura | B60W 30/00 |
| | | | 701/2 |

OTHER PUBLICATIONS

Mueller, Florian "Floyd"; Muirhead; Matthew, "Jogging with a Quadcopter," Exertion Game Lab, RMIT University, Melbourne Australia, CHI 2015, Apr. 18-23, 2015, Seoul, Republic of Korea.

* cited by examiner

Predicting the future location of the user based on a pace of the user — 401

FIGURE 4

Generating the target location based on the pace of the user — 501

FIGURE 5

Determining the pace of the user based on recorded historical measurements of the user's pace over defined time intervals within a threshold distance of a present location of the user — 601

FIGURE 6

Determining the pace of the user based on a mathematical combination of heart rates indicated by at least two of the plurality of heart rate messages that were previously received — 701

FIGURE 7

Scaling the pace of the user by a weighting factor defined based on whether the heart rates have increased or decreased over a defined time interval — 801

FIGURE 8

METHODS AND DEVICES FOR HEART RATE CONTROLLING DRONES

BACKGROUND

The present inventive concepts generally relate to controlling a drone.

Running is a global trend that is popular as an exercise routine to improve health, stamina, and general well being of individuals. A multi-billion dollar industry related to running has developed that includes shoes, clothes, wearable devices, fitness tracking devices, apps, etc. In parallel, an industry related to drones has developed. Drones may be an integral part of the future Internet of Things (IoT) enabled world that assist individuals with tasks such as monitoring, filming, cleaning, repairs, and security. These two industries, namely running and drones, may be combined such that drones may be used to improve the experiences of runners in a variety of settings.

SUMMARY

Some embodiments of the present disclosure are directed to a method of controlling a drone by performing various operations on a processor configured to control location of the drone. These operations may include receiving a plurality of heart rate messages from a remote device carried by a user, each heart rate message of the plurality of heart rate messages including heart rate information of the user, and/or receiving a plurality of location messages from the remote device carried by the user, each location message of the plurality of location messages including location information of the user. The operations on the processor may include predicting a future location of the user based on the heart rate messages and the location messages, generating a target location to which the drone is to be moved based on the future location of the user, and/or commanding the drone to move to the target location.

According to various embodiments, predicting the future location of the user based on the heart rate messages and the location messages may include predicting the future location of the user based on differences in the heart rate information in at least two of the heart rate messages and differences in the location information in at least two of the location messages. Predicting the future location of the user may include predicting the future location of the user based on a pace of the user. Generating a target location to which the drone is to be moved may include generating the target location based on the pace of the user.

According to various embodiments, the operations on the processor may include determining the pace of the user based on recorded historical measurements of the user's pace over defined time intervals within a threshold distance of a present location of the user. The operations may include determining the pace of the user based on a mathematical combination of heart rates indicated by at least two of the plurality of heart rate messages that were previously received. Operations may include scaling the pace of the user by a weighting factor defined based on whether the heart rates have increased or decreased over a defined interval.

According to various embodiments, the operations on the processor may include receiving environment information associated with the location information of the user, and/or determining an adjusted pace of the user based on the environment information and the pace of the user. Predicting the future location of the user further may include predicting the future location of the user based on the adjusted pace. The environment information may include weather conditions, terrain information, geographical features, and/or a location of another user. The environment information may indicate presence of persons in a proximity of the user based on detecting radio frequency signals received from devices carried by the persons. The method may include scaling the adjusted pace of the user by a weighting factor in response to determining the presence of persons in the proximity of the user.

According to various embodiments, the operations on the processor may include determining, based on the differences in the heart rate information, that the user is maintaining a steady heart rate, determining, based on the differences in the location information, that the user is stationary, and/or controlling the location of the drone to be stationary based on the determining that the user is maintaining a steady heart rate and the determining that the user is stationary. The operations may include determining, based on the differences in the heart rate information, that the user is accelerating or decelerating, predicting, based on the determining that the user is accelerating or decelerating, the future location of the user, and/or controlling a speed of the drone based on the determining that the user is accelerating or decelerating and the predicting the future location of the user. In some embodiments, determining, based on the differences in the heart rate information, that the user is accelerating or decelerating may include determining that the user is accelerating based on a first heart rate information of one of the plurality of heart rate messages being greater than a second heart rate information of a previous one of the plurality of heart rate messages, and/or determining that the user is decelerating based on the first heart rate information being less than the second heart rate information. The controlling the speed of the drone may be based on the determining that the user is accelerating or decelerating by performing operations including increasing the speed of the drone as the drone travels to the future location of the user that was predicted, in response to the determining that the user is accelerating, and/or decreasing the speed of the drone as the drone travels to the future location of the user that was predicted, in response to the determining that the user is decelerating.

According to various embodiments, the operations may include providing an input to a camera associated with the drone, in response to the predicting the future location of the user based on the differences in the heart rate information and the differences in the location information. The method may include controlling a zoom of the camera, in response to the predicting the future location of the user based on the differences in the heart rate information and the differences in the location information. Controlling the zoom of the camera may include determining, based on differences in the heart rate information in at least two of the heart rate messages, that the user is accelerating or decelerating, decreasing the zoom of the camera responsive to determining that the user is accelerating, and/or increasing the zoom of the camera responsive to determining that the user is decelerating.

According to various embodiments, the operations may include adjusting a field of view of the camera, in response to predicting the future location of the user based on the differences in the heart rate information and the differences in the location information. Adjusting the field of view of the camera further may include determining, based on differences in the heart rate information in at least two of the heart rate messages, that the user is accelerating or decelerating, increasing the field of view of the camera responsive to determining that the user is accelerating, and/or decreasing the field of view of the camera responsive to determining that the user is decelerating. Controlling the location of the drone may include providing information related to the altitude, speed, yaw, roll, pitch, and/or heading of the drone.

Other methods and devices, according to embodiments of the present disclosure will be or become apparent to one with skill in the art upon review of the following drawings and detailed description. It is intended that all such methods and devices be included within this description, be within the scope of the present inventive subject matter, and be protected by the accompanying claims.

BRIEF DESCRIPTION OF THE DRAWINGS

Other features of embodiments will be more readily understood from the following detailed description of specific embodiments thereof when read in conjunction with the accompanying drawings, in which:

FIGS. 2 to 19 are flowcharts of operations for controlling a drone in accordance with some embodiments of the present disclosure.

DETAILED DESCRIPTION

Various embodiments will be described more fully hereinafter with reference to the accompanying drawings. Other embodiments may take many different forms and should not be construed as limited to the embodiments set forth herein. Like numbers refer to like elements throughout. Numerous specific details are set forth in order to provide a thorough understanding of embodiments of the present inventive concepts. However, it will be understood by those skilled in the art that the present invention may be practiced without these specific details. In other instances, well-known methods, procedures, components and circuits have not been described in detail so as not to obscure the present invention. It is intended that all embodiments disclosed herein can be implemented separately or combined in any way and/or combination.

As noted above, running is a popular leisure activity for active individuals who seek to improve their health. Maintaining a good pace and/or maintaining a particular heart rate are goals of many runners. Drones may be able to assist runners improve their experience. Various embodiments described herein may arise from a recognition for a need to improve the experience of runners using drones to provide guidance regarding pacing, direction, filming, etc. The location and/or heart rate of the runner may be used to control the location of the drone such that the drone moves to a position suitable to the runner.

Figure 1:
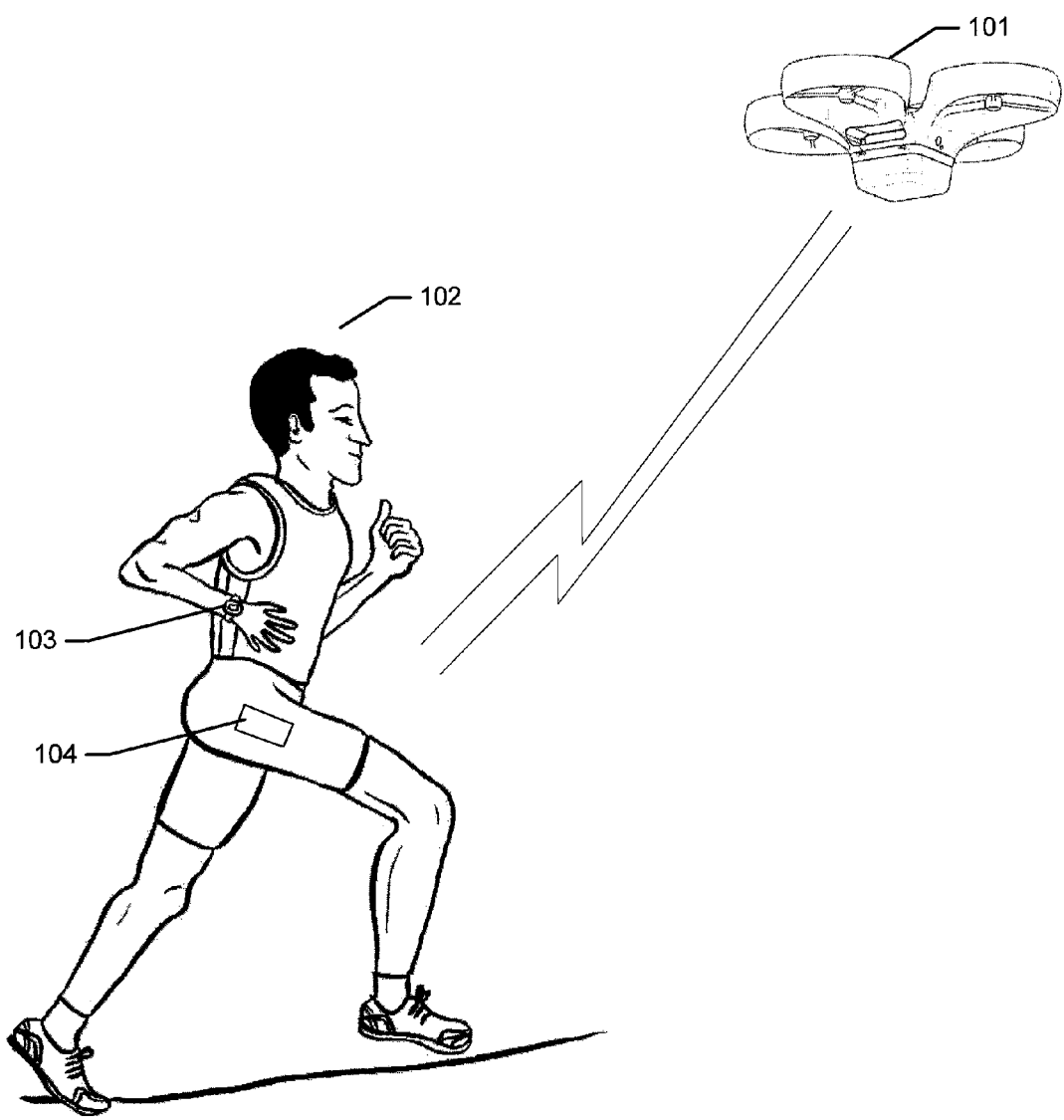
FIG. 1 illustrates a runner guided by a drone in accordance with some embodiments of the present disclosure.

Referring now to FIG. 1, a runner (i.e. user) 102 is illustrated in view of a drone 101 that assists and/or guides the runner. The runner 102 may be carrying a remote device 103 that is remote from the drone 101. The remote device 103 may measure the heart rate of the user 102 and/or may determine the location of the user by use of GPS information. Although illustrated as a watch-like device worn on the wrist of the user 102, the remote device 103 may be part of or in communication with a mobile device 104 carried in the pocket of the user, on a belt clip, or in an armband. In some embodiments, the mobile device 104 may perform the functions described herein. The remote device 103 may also include a chest strap worn by the user 102 for accurate pulse measurements. In some embodiments, the remote device 103 may include a separate pulse monitoring device that is separate from a location tracking device associated with the user 102. In some embodiments, the pulse monitor device may be co-located with the drone 101 and may be configured to remotely measure the pulse using an infrared (IR) camera and/or by analyzing color changes or motion changes related to the pulse of the user 102.

Figure 2:
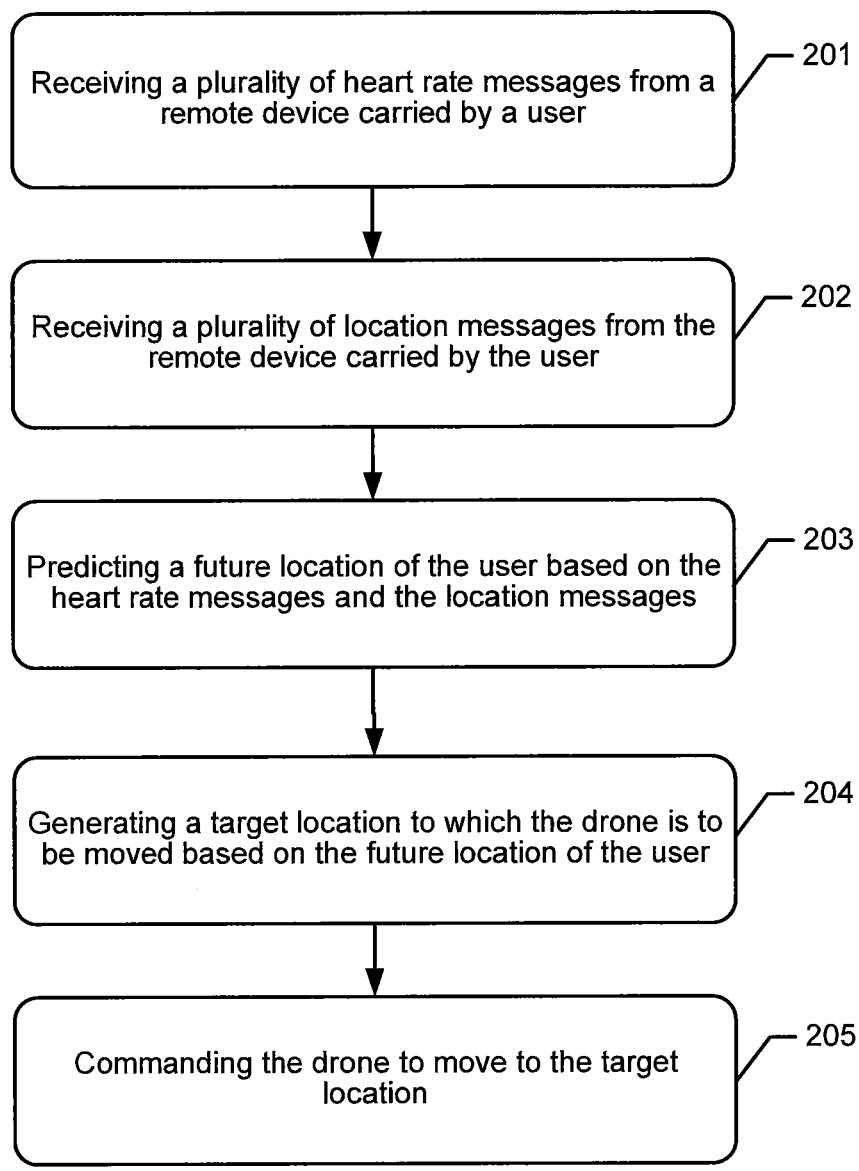

Referring to FIG. 2, a flowchart of operations that may be performed to control the drone 101 of FIG. 1 is illustrated. These operations may be executed by a processor in the remote device 103 associated with the user, another device associated with the user, and/or by a processor in the drone 101. In some embodiments, these operations may be performed by an application in the remote device 103 and/or in an associated mobile device 104 carried by the user. Resulting information regarding a target location may be communicated to the drone 101 by a wireless link from the remote device 103 and/or mobile device 104 of FIG. 1. As illustrated in FIG. 2, at block 201, a plurality of heart rate messages may be received by a remote device 103 and/or a mobile device 104 carried by the user 102. A plurality of location messages may be received from the remote device 103 and/or mobile device 104 of FIG. 1 at block 202. The location information and the heart rate information may be in a single message or in different messages, in various embodiments. Although discussed herein in the context of heart rate messages and/or location messages, heart rate information and/or location information may be received in any form of communication from the remote device 103 and/or a mobile device 104 carried by the user 102.

Still referring to FIG. 2, at block 203, a future location of the user may be predicted based on the heart rate messages and the location messages. A target location to which the drone is to be moved may be generated at block 204, based on the future location of the user. At block 205, the drone may be commanded to move to the target location that was generated. Commanding the drone to move to the target location may include generating information related to the altitude, speed, yaw, roll, pitch, and/or heading to which the drone is to reposition.

Although the discussion herein is based on, for example, control of a drone based on heart rate information, other measurements of physical performance may be used in addition to, or in lieu of, the heart rate measurements. For example, heart rate variability, blood pressure, blood oxygen level, breathing rate, pulse, perspiration, hemoglobin level, electromyography (EMG), electrodermal activity (EDA), skin conductance, galvanic skin response (GSR), electrodermal response (EDR), psychogalvanic reflex (PGR), skin conductance response (SCR), skin conductance level (SCL), and/or other physiological measurements may be used to control the drone. Sensors for brain activity related to exercise performance and/or motivation such as electroencephalogram (EEG), functional magnetic resonance imaging or functional MRI (fMRI), Electrocorticography (ECoG), or intracranial electroencephalography (iEEG), diffusion MRI (dMRI), and/or near-infrared spectroscopy (NIRS) may be used to control the drone.

Figure 3:
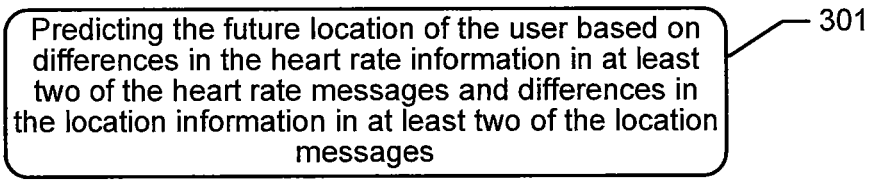

Referring now to FIG. 3, the future location of the user may be predicted, based on differences in the heart rate information in at least two of the heart rate messages and/or differences in the location information in at least two of the location messages. For example, the heart rate in a recent heart rate message N may be compared to the heart rate in a previous message N−1. Similar comparisons may be made with location information in location messages N and N−1. The present inventive concepts may be extended to the heart rate at N−2, N−3, etc. Based on these two or more samples of the heart rate of the user and/or the location of the user, a pace of the user may be determined. Although consecutive messages N and N−1 are described as an example, any two messages with heart rate and/or location information may be used for determine the differences. In some embodiments, a targeted pace may be set as desired by the user and used for predicting the future location of the user.

Now referring to FIG. 4, based on two or more samples of the heart rate and/or location of the user, the future location of the user may be predicted based on the pace of the user, at block 401. Referring to FIG. 5, the target location may be generated based on the pace of the user, at block 501. The target location may be a location to which the drone is to move such that the user may follow the drone to maintain a present pace or change to a target pace. In some embodiments, the drone may move to a location in order to increase or decrease the heart rate of the user, based on an optimum training pace of the user or based on a goal of the user. The target location may be determined to provide a suitable view from a camera associated with the drone for purposes of filming.

Referring now to FIG. 6, based on recorded historical measurements of the user's pace over defined time intervals, the pace of the user may be determined, at block 601. The pace may be determined based on two or more time intervals within which a user travels at least a threshold distance from the present location of the user. In some embodiments, a historical pace in a particular geographic region may be used to set a target pace that the user strives to achieve. Referring now to FIG. 7, the pace of the user may be determined based on a mathematical combination of heart rates indicated by at least two of the plurality of heart rate messages that were previously received, at block 701. The mathematical combination of heart rates may include averaging two or more heart rate measurements, removing outlier heart rate values, and/or determining a mode of a plurality of heart rate values.

Referring now to FIG. 8, the pace of the user may be scaled by a weighting factor that is defined based on whether the heart rates have increased or decreased over a defined time interval, at block 801. In other words, the pace of the user may be determined to have accelerated by determining that the heart rates have increased over a defined time interval. Similarly, the peace of the user may be determined to have decelerated in determining that the heart rates have decreased over a defined time interval. The pace of the user may be scaled upward by a weighting factor after a threshold number of increased heart rate values are received. The pace of the user may scaled downward by a weighting factor after a threshold number of decreased heart rate values are received.

Figure 9:
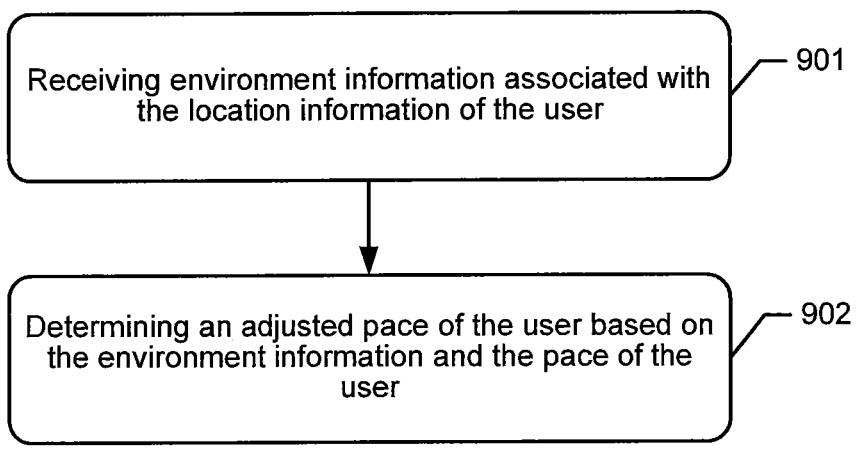

Referring now to FIG. 9, environment information associated with the location information of the user may be received, at block 901. At block 902, an adjusted pace of the user may be determined based on the environment information and/or the pace of the user. The future location may be predicted based on the adjusted pace of the user. The environment information may include weather conditions, terrain information, geographical features, and/or the location of one or more other users. For example, if weather information for the location of the user indicates that it is raining, the adjusted pace of the user may be reduced to take into account difficulty in running on a wet surface, poorer visibility, and/or an added weight of wet clothes. In some embodiments, geographical features such as rocky or sandy running terrain may be determined and use as input to a computation to affect the adjusted pace of the user since these surfaces may offer poorer traction/footing for the user. Other geographical features such as a parking lot may provide a lot of roadblocks for the runner when the parking lot has many cars, slowing the pace. On the other hand, the day of the week or the time of day may also be taken into account. For example, a parking lot may be almost full during business hours on weekdays but may be almost completely empty on a Sunday. The pace of the runner may be adjusted based on information related to the time of day and/or day of the week in conjunction with the heart rate information.

According to various embodiments, once the heart rate is obtained, it may be determined if the heart rate should be increased, decreased, and/or maintained at the current level. The environment of the user may be analyzed as previously discussed. A user's heading may be determined based on the current location/heading of the user, a predetermined route for the user, and/or based on a probability that the user will follow the predetermined route. The probability that the user will follow the predetermined route may be affected by factors related to the environment information. The drone may be commanded to increase speed in order to increase the user's heart rate, maintain a current speed to keep a current pace and/or heart rate, and/or decrease speed in order to decrease the heart rate. The drone may be commanded to decrease speed based on environment information such as, for example, if a hill is approaching but the heart rate of the user needs to be maintained.

Figure 10:
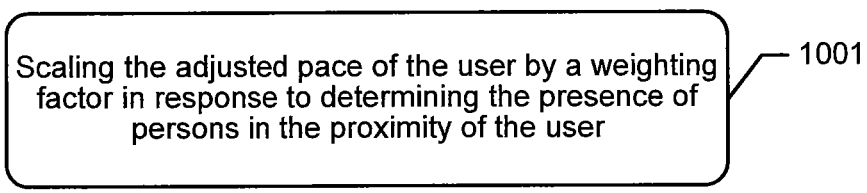

Referring now to FIG. 10, the environment information may indicate the presence of persons in a proximity of the user based on detecting radio frequency signals received by the mobile device 104 from devices carried by the other persons. In some embodiments, an indication of presence of persons in the proximity of the user may be received from a network. A density of other users may indicate runners in a race or a high pedestrian traffic area. The adjusted pace of the user may be scaled by a weighting factor in response to determining at least a threshold number of mobile devices from which RF signals are detected in the proximity of the user, at block 1001.

Figure 11:
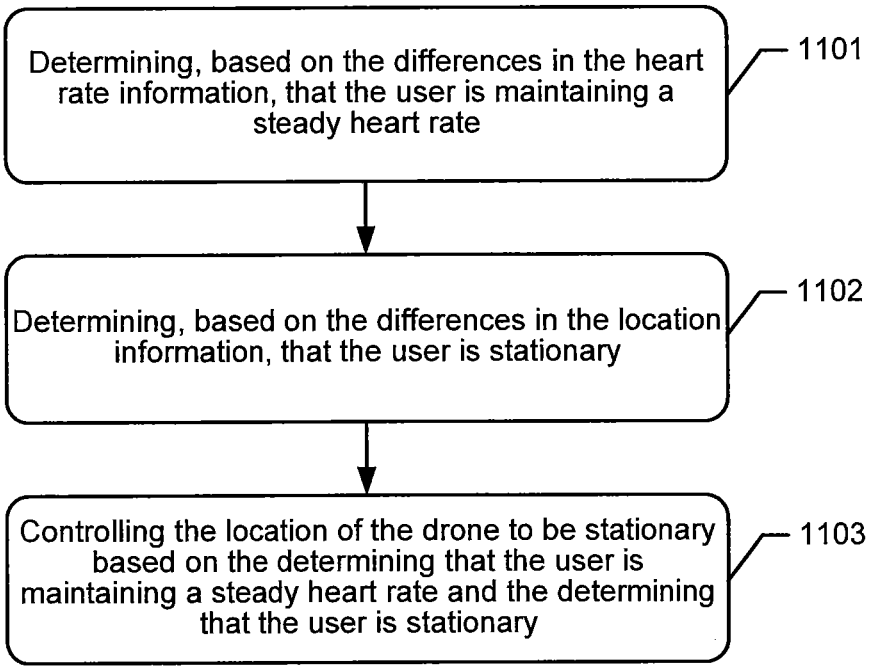

In some embodiments, a traffic light or crosswalk may be in the path of the runner. Referring now to FIG. 11, based on the differences in the heart rate information, it may be determined that the user is maintaining a steady heart rate, at block 1101. Based on different samples of location information, it may be determined that the user is stationary, at block 1102. For example, a runner may be at a traffic light but is jogging in place to maintain a steady heart rate. At block 1103, the location of the drone may be controlled to be stationary based on determining that the user is maintaining a steady heart rate and determining that the user is stationary. The drone may be instructed to move once it is determined that the user is no longer stationary.

Figure 12:
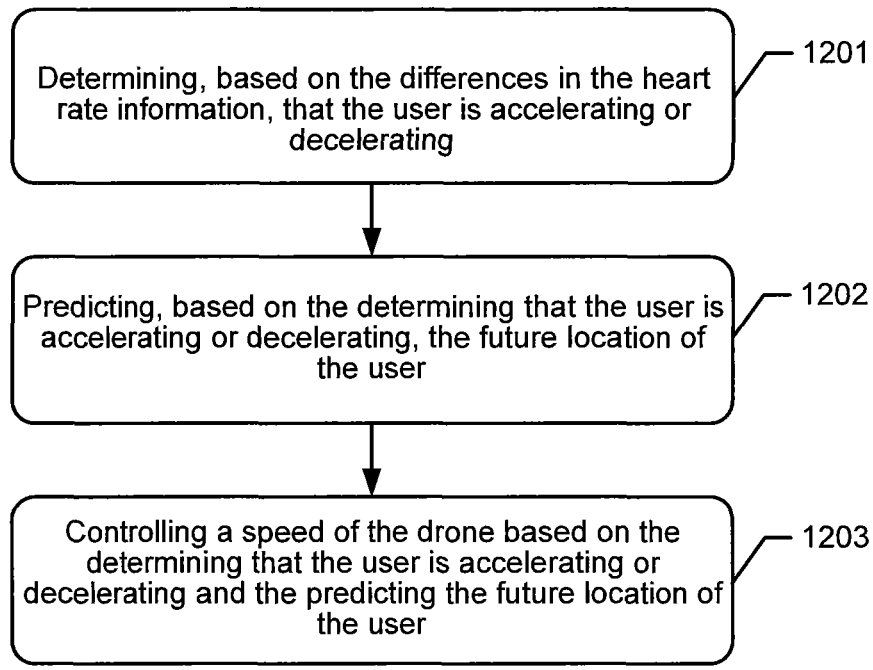

Heart rate and/or location information may be used to determine that a runner is accelerating or decelerating. Acceleration and deceleration may be due to hills and/or inclines/declines in the running course. Acceleration and deceleration of the heart rate may occur due to changes in the energy level of the runner at different points during the run. Referring now to FIG. 12, based on the differences in the heart rate information, it may be determined that the user is accelerating or decelerating, at block 1201. The future location of the user may be estimated based on the recognition that the user is accelerating or decelerating, at block 1202. The speed of the drone may be controlled based on the determination that the user is accelerating or decelerating and the predicted future location of the user, at block 1203.

Figure 13:
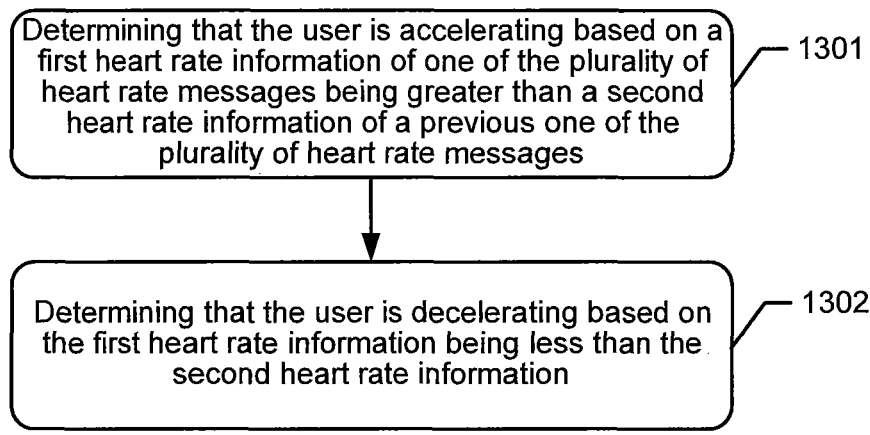

Referring now to FIG. 13, determining that the user is accelerating or decelerating based on the differences in the heart rate information may include determining that the user is accelerating based on a heart rate information of a given heart rate message being greater than the heart rate information of a previous one or more of the heart rate messages, at block 1301. The user may be decelerating if it is determined that the heart rate information of a given heart rate message is less than the heart rate information of a previous one or more of the heart rate messages, at block 1302.

Figure 14:
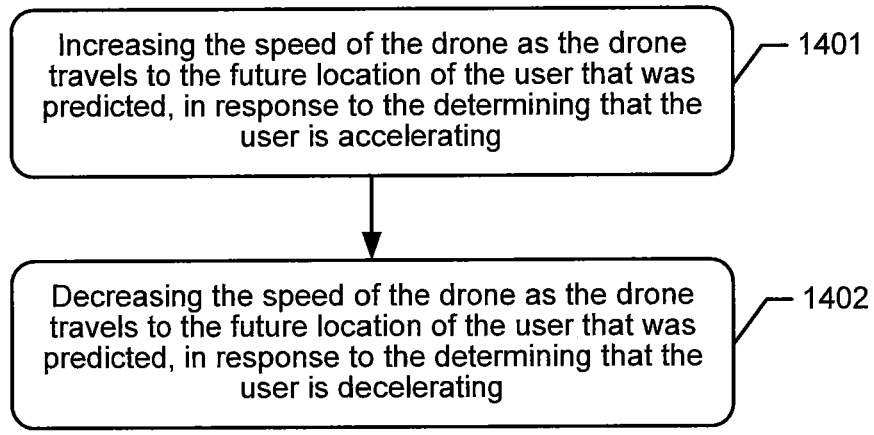

Referring now to FIG. 14, the speed of the drone may be controlled based on the determining that the user is accelerating or decelerating. The speed of the drone may be increased as the drone travels to the future location of the user that was predicted, if it is determined that the user is accelerating, at block 1401. The speed of the drone may be decreased as the drone travels to the future location of the user that was predicted, if it is determined that the user is decelerating, at block 1402.

The drone may be controlled to move smoothly, controlled to maintain a defined distance and/or azimuth angle relative to the user by controlling the drone based on the heart rate. For example, the user can be expected to be able to have greater likelihood of high acceleration in speed when the user's heart rate is below a defined threshold. In contrast, the user can be expected to have a greater likelihood of deceleration in speed when the user's heart rate is above a defined threshold. In some embodiments, upper and/or lower threshold heart rate values may be defined in order to command the drone to increase or decrease distance from the user. If a heart rate measurement is above an upper threshold heart rate, the drone may be commanded to decrease distance between the user and the drone since it is anticipated that the user has increased speed but will not be able to sustain the higher speed and will soon decelerate. If a heart rate measurement is below a lower threshold heart rate, the drone may be commanded to increase distance between the user and the drone since it is anticipated that the user has decreased speed and will have reserve energy to be able to accelerate in the near future.

Figure 15:
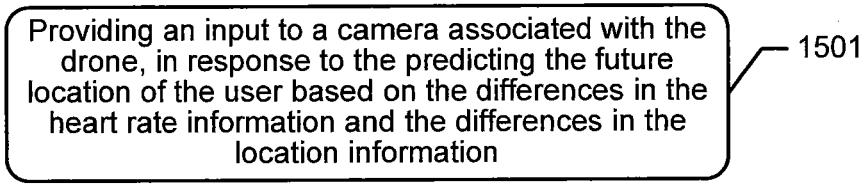
Figure 16:
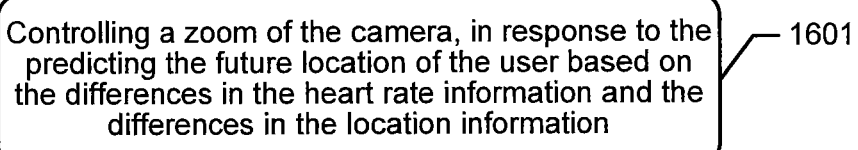
Figure 17:
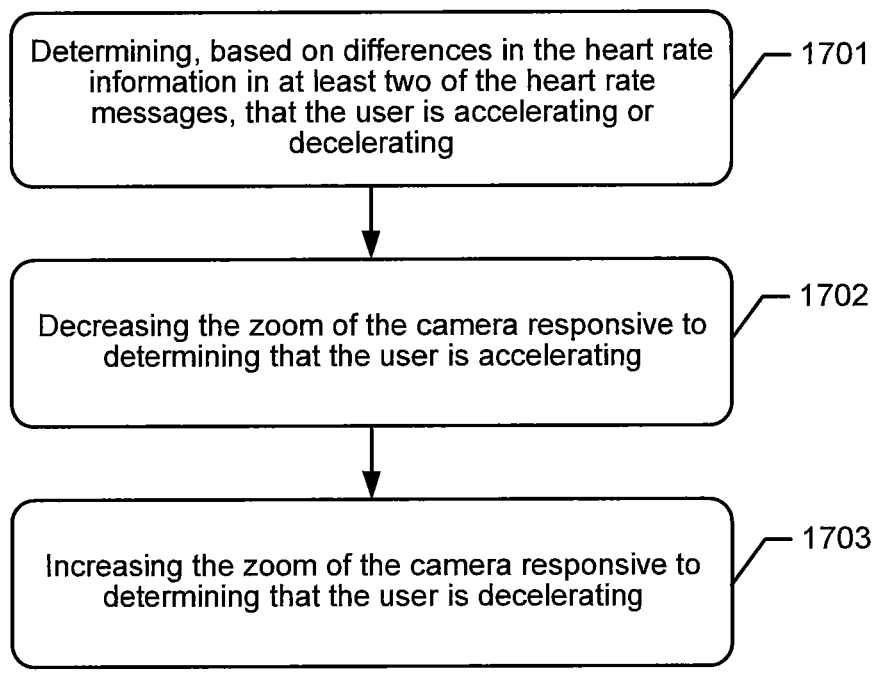

In some embodiments, a camera associated with the drone may be controlled based of the heart rate of the user. Referring now to FIG. 15, an input to a camera associated with the drone may be provided, in response to predicting the future location of the user based on the differences in the heart rate information and/or the differences in the location information, at block 1501. Referring now to FIG. 16, a zoom of the camera may be controlled, in response to predicting the future location of the user based on the differences in the heart rate information and/or the differences in the location information, at block 1601. Referring now to FIG. 17, the zoom of the camera may be controlled to maximize the view of the runner. Based on differences in the heart rate information in at least two of the heart rate messages, it may be determined that the user is accelerating or decelerating, at block 1701. The zoom of the camera may be decreased, if the user is accelerating, at block 1702. The zoom of the camera may be increased, if the user is decelerating, at block 1703. In other words, if the runner is slowing down, a closer view of the runner may be possible by adjusting the zoom of the camera.

Figure 18:
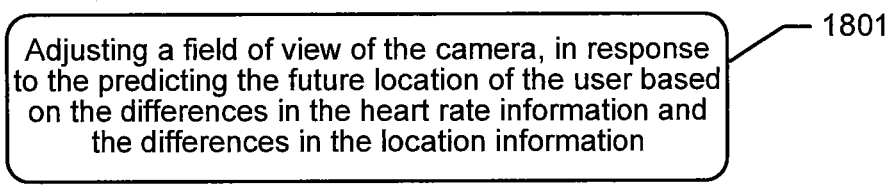
Figure 19:
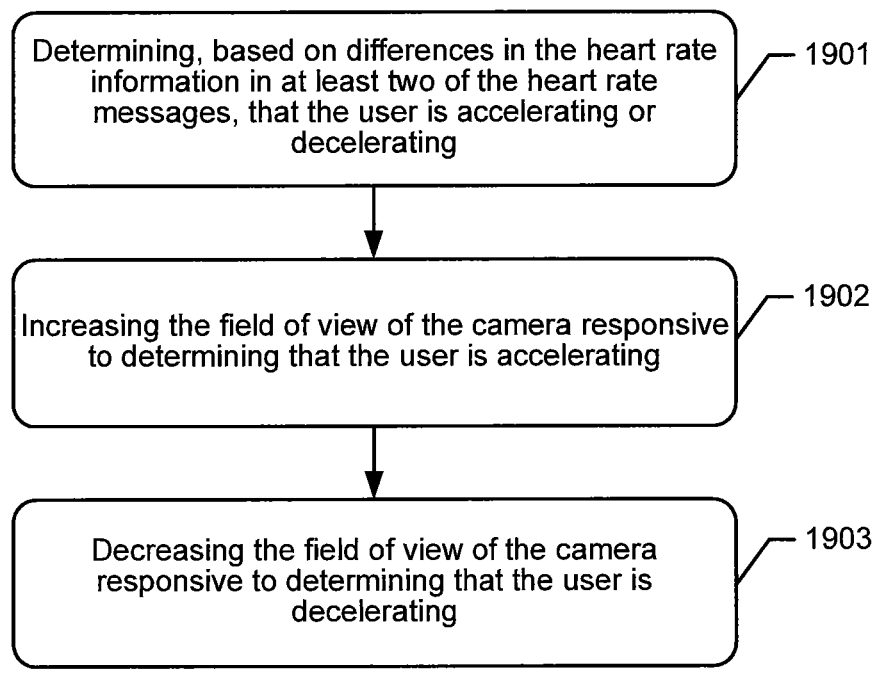

In some embodiments, the field of view of a camera associated with the drone may be adjusted based of the heart rate of the user. The field of view, also referred to as "angle of view (AOV)", describes the angular extent of a given scene that is imaged by the camera. Referring now to FIG. 18, the field of view of the camera may be adjusted, in response to the predicting the future location of the user based on the differences in the heart rate information and/or the differences in the location information, at block 1801. Referring now to FIG. 19, adjusting the field of view of the camera may include determining, based on differences in the heart rate information in at least two of the heart rate messages, that the user is accelerating or decelerating, at block 1901. The field of view of the camera may be increased if the user is accelerating, at block 1902. The field of view of the camera may be decreased if the user is decelerating, at block 1903.

As discussed herein, the heart rate allows prediction of how quickly the user may speed up. The drone can be repositioned to allow the user to stay within the field of view of the camera if the predicted speed-up occurs. Due to the inaccuracy of determining GPS location by mobile devices over small distances (for example, 15 feet), controlling a drone based on GPS location alone can lead to erratic control movements and result in the drone not being properly positioned to provide a target distance and/or azimuth angle relative to the direction of movement of the user. When the drone is photographing or capturing video of the user, there is a risk that the user will leave the field of view of the camera. Moreover, erratic control of the drone can result in undesirable erratic movement of the camera. Embodiments of the present disclosure use the heart rate of the person to predict that the person is likely to accelerate or decelerate in order to improve control of the drone.

Figure 20:
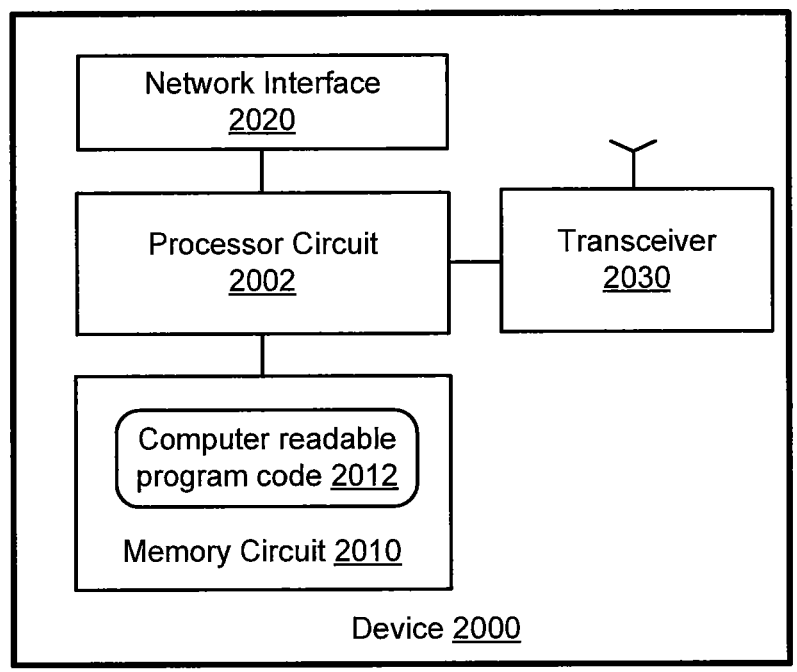
FIG. 20 is a block diagram of a device configured to perform operations according to the flowcharts of FIGS. 2 to 19, according to some embodiments of the present disclosure.

FIG. 20 is a block diagram of a device 2000, for use in conjunction with drone 101 of FIG. 1, that is configured according to one or more embodiments disclosed herein. The device 2000 can include a transceiver 2030, a network interface 2020, a processor circuit 2002, and a memory circuit 2010 containing computer readable program code 2012.

The transceiver 2030 is configured to communicate with the drone 101 of FIG. 1 using one or more of the radio access technologies. The processor circuit 2002 may include one or more data processing circuits, such as a general purpose and/or special purpose processor, e.g., microprocessor and/or digital signal processor, that may be collocated or distributed across one or more networks. The processor circuit 2002 (also referred to as a processor) is configured to execute the computer readable program code 2012 in the memory 2010 to perform at least some of the operations and methods of described herein as being performed by the device 2000. For example, processor 2002 may be configured to perform operations discussed above with respect to FIGS. 2-19. The network interface 2020 communicates with other devices 2000, a drone 101, a remote device 103, and/or a mobile device 104 carried by the user 102 of FIG. 1.

Figure 21:
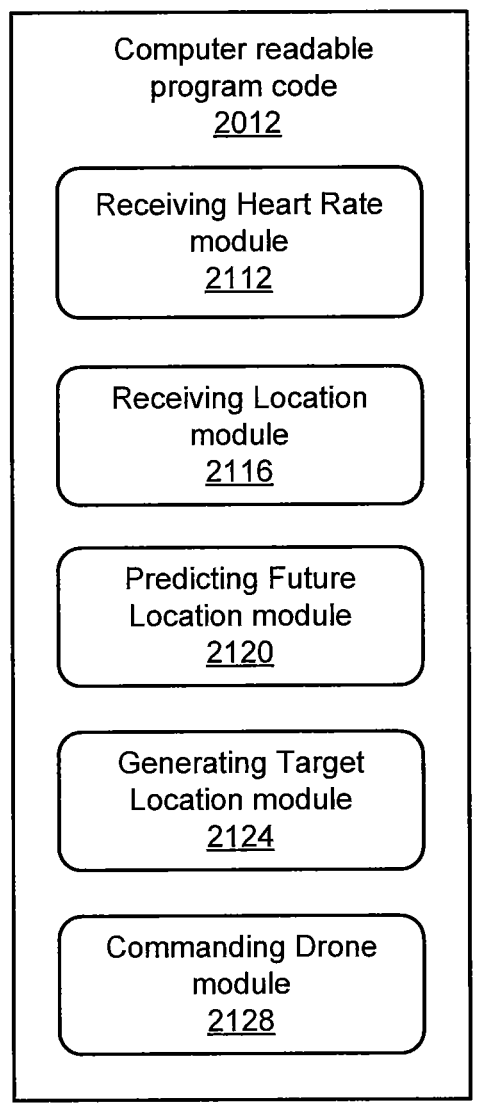
FIG. 21 is a block diagram of a computer readable program code for performing operations according to the flowcharts of FIGS. 2 to 19, according to some embodiments of the present disclosure.

FIG. 21 illustrates the computer readable program code 2012 in more detail. In particular, the computer readable program code 2012 includes a receiving heart rate module 2112, a receiving location module 2116, a predicting future location module 2120, a generating target location module 2124, and/or a commanding drone module 2128 for commanding the drone 101 of FIG. 1 to move to the target location.

Further Definitions and Embodiments

In the above-description of various embodiments of the present inventive concepts, aspects of the present inventive concepts may be illustrated and described herein in any of a number of patentable classes or contexts including any new and useful process, machine, manufacture, or composition of matter, or any new and useful improvement thereof. Accordingly, aspects of the present inventive concepts may be implemented in entirely hardware, entirely software (including firmware, resident software, micro-code, etc.) or combining software and hardware implementation that may all generally be referred to herein as a "circuit," "module," "component," or "system." Furthermore, aspects of the present inventive concepts may take the form of a computer program product comprising one or more computer readable media having computer readable program code embodied thereon.

Any combination of one or more computer readable media may be used. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

Computer program code for carrying out operations for aspects of the present inventive concepts may be written in any combination of one or more programming languages, including an object oriented programming language such as Java, Scala, Smalltalk, Eiffel, JADE, Emerald, C++, C#, VB.NET, Python, etc., conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the device, partly on the device, as a stand-alone software package, partly on the device and partly on a remote computer or entirely on the remote computer or server. In the latter scenario, the remote computer may be connected to the device through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Aspects of the present inventive concepts are described herein with reference to flowchart illustrations and/or block diagrams of methods, apparatus (device), and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It is to be understood that the terminology used herein is for the purpose of describing particular embodiments only and is not intended to be limiting to other embodiments. Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

The flowchart and block diagrams in the Figures illustrate the architecture, functionality, and operation of possible implementations of systems, methods, and computer program products according to various aspects of the present inventive concepts. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Spatially relative terms, such as "beneath," "below," "lower," "above," "upper", "top", "bottom" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular aspects only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Like reference numbers signify like elements throughout the description of the Figures.

The corresponding structures, materials, acts, and equivalents of any means or step plus function elements in the claims below are intended to include any disclosed structure, material, or act for performing the function in combination with other claimed elements as specifically claimed. The description of the present inventive concepts has been presented for purposes of illustration and description, but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described in order to best explain the principles of the disclosure and the practical application, and to enable others of ordinary skill in the art to understand the disclosure with various modifications as are suited to the particular use contemplated.

In the drawings and specification, there have been disclosed typical embodiments and, although specific terms are employed, they are used in a generic and descriptive sense only and not for purposes of limitation, the scope of the disclosure being set forth in the following claims.

The invention claimed is:

1. A method of controlling a drone, the method comprising:
    performing operations as follows on a processor configured to control location of the drone:
    receiving a plurality of heart rate messages from a remote device carried by a user, each heart rate message of the plurality of heart rate messages comprising heart rate information of the user;
    receiving a plurality of location messages from the remote device carried by the user, each location message of the plurality of location messages comprising location information of the user;
    determining, based on the plurality of location messages, a current speed of the user;
    determining, based on the current speed of the user and based on the plurality of heart rate messages, a target speed of the drone; and
    commanding the drone to move at the target speed of the drone.

2. The method of claim 1, wherein the determining the target speed of the drone comprises:
    determining the target speed of the drone based on differences in the heart rate information in at least two of the heart rate messages and based on the current speed.

3. The method of claim 1, wherein the determining the target speed of the drone comprises:
    determining the pace of the user based on recorded historical measurements of the user's pace over defined time intervals within a threshold distance of a present location of the user; and
    determining the target speed of the drone based on the pace of the user.

4. The method of claim 3, further comprising:
    scaling the pace of the user by a weighting factor based on a comparison of a heart rate indicated by at least one of the plurality of heart rate messages to a threshold heart rate.

5. The method of claim 3, further comprising:
    scaling the pace of the user by a weighting factor defined based on whether the heart rates have increased or decreased over a defined time interval.

6. The method of claim 3, further comprising:
    receiving environment information associated with the location information of the user; and
    determining an adjusted pace of the user based on the environment information and the pace of the user,
    wherein the determining the target speed of the drone further comprises determining the target speed of the drone based on the adjusted pace of the user.

7. The method of claim 6, wherein the receiving the environment information comprises determining weather conditions, terrain information, geographical features, and/or a location of another user.

8. The method of claim 6, wherein the environment information indicates presence of persons in a proximity of the user based on detecting radio frequency signals received from devices carried by the persons, the method further comprising:
  scaling the adjusted pace of the user by a weighting factor in response to determining the presence of persons in the proximity of the user.

9. The method of claim 1, further comprising:
  determining, based on differences in the heart rate information in at least two of the heart rate messages, that the user is maintaining a steady heart rate;
  determining, based on the differences in the location information in at least two of the location messages, that the user is stationary; and
  controlling the target speed of the drone to be stationary based on the determining that the user is maintaining a steady heart rate and the determining that the user is stationary.

10. The method of claim 1, further comprising:
  determining, based on the differences in the heart rate information in at least two of the heart rate messages, that the user is accelerating or decelerating;
  predicting, based on the determining that the user is accelerating or decelerating, a future speed of the user; and
  controlling the target speed of the drone based on the determining that the user is accelerating or decelerating and the future speed of the user that was predicted.

11. The method of claim 1, further comprising:
  controlling a zoom of the camera, in response to the determining, the target speed of the drone.

12. The method of claim 1, further comprising:
  adjusting a field of view of the camera, in response to the determining the target speed of the drone.

13. A method of controlling a drone, the method comprising:
  performing operations as follows on a processor configured to control location of the drone:
  receiving a plurality of heart rate messages from a remote device carried by a user, each heart rate message of the plurality of heart rate messages comprising heart rate information of the user;
  receiving a plurality of location messages from the remote device carried by the user, each location message of the plurality of location messages comprising location information of the user;
  determining, based on the plurality of location messages, a current speed of the user;
  determining, based on the current speed of the user and based on the plurality of heart rate messages, a target speed of the drone;
  generating a target location to which the drone is to be moved based on the target speed of the drone; and
  commanding the drone to move to the target location.

14. The method of claim 13,
  wherein the determining the target speed of the drone comprises determining the target speed of the drone based on a pace for the user determined based on recorded historical measurements of the user's pace over defined time intervals within a threshold distance of a present location of the user, and
  wherein the generating a target location to which the drone is to be moved comprises generating the target location based on the pace of the user.

15. The method of claim 14, further comprising:
  receiving environment information associated with the location information of the user; and
  determining an adjusted pace of the user based on the environment information and the pace of the user,
  wherein the determining the target speed of the drone comprises determining the target speed of the drone based on the adjusted pace, and
  wherein the receiving the environment information comprises determining weather conditions, terrain information, geographical features, and/or a location of another user.

16. The method of claim 13, further comprising:
  providing an input to a camera associated with the drone, in response to the generating the target location to which the drone is to be moved.

17. The method of claim 13, further comprising:
  controlling a zoom of the camera, in response to the generating the target location to which the drone is to be moved.

18. The method of claim 17, wherein the controlling the zoom of the camera comprises:
  determining, based on differences in the heart rate information in at least two of the heart rate messages, that the user is accelerating or decelerating;
  decreasing the zoom of the camera responsive to determining that the user is accelerating; and
  increasing the zoom of the camera responsive to determining that the user is decelerating.

19. The method of claim 13, further comprising:
  adjusting a field of view of the camera, in response to the generating the target location to which the drone is to be moved.

20. A device for controlling a position of the drone, wherein the device comprises a processor configured to perform operations comprising:
  receiving a plurality of heart rate messages from a remote device carried by a user, each heart rate message of the plurality of heart rate messages comprising heart rate information of the user;
  receiving a plurality of location messages from the remote device carried by the user, each location message of the plurality of location messages comprising location information of the user;
  determining, based on the plurality of location messages, a current speed of the user;
  determining, based on the current speed of the user and based on the plurality of heart rate messages, a target speed of the drone; and
  commanding the drone to move at the target speed of the drone.

* * * * *